(12) United States Patent
Otsuka et al.

(10) Patent No.: US 9,541,534 B2
(45) Date of Patent: Jan. 10, 2017

(54) INSPECTION APPARATUS FOR ARTICLE STORAGE FACILITY

(71) Applicant: Daifuku Co., Ltd., Osaka-shi (JP)

(72) Inventors: Hiroshi Otsuka, Gamo-gun (JP); Shinsuke Kawamura, Gamo-gun (JP); Tadahiro Yoshimoto, Gamo-gun (JP)

(73) Assignee: Daifuku Co., Ltd., Osaka-shi (JP)

( * ) Notice: Subject to any disclaimer, the term of this patent is extended or adjusted under 35 U.S.C. 154(b) by 202 days.

(21) Appl. No.: 14/308,158

(22) Filed: Jun. 18, 2014

(65) Prior Publication Data

US 2015/0000372 A1    Jan. 1, 2015

(30) Foreign Application Priority Data

Jun. 26, 2013 (JP) .................. 2013-134265

(51) Int. Cl.
| | |
|---|---|
| *G01N 33/00* | (2006.01) |
| *H01L 21/673* | (2006.01) |
| *H01L 21/677* | (2006.01) |
| *H01L 21/67* | (2006.01) |

(52) U.S. Cl.
CPC ..... *G01N 33/0009* (2013.01); *H01L 21/67769* (2013.01); *H01L 21/67253* (2013.01); *H01L 21/67393* (2013.01)

(58) Field of Classification Search
CPC ....................... G01N 33/0009; H01L 21/67769
USPC .......................................... 33/533, 613, 645
See application file for complete search history.

(56) References Cited

U.S. PATENT DOCUMENTS

| | | | |
|---|---|---|---|
| 9,257,320 B2 * | 2/2016 | Fosnight | ........... H01L 21/67775 |
| 2004/0191032 A1 * | 9/2004 | Foulke | ..................... B65G 1/04 |
| | | | 414/280 |
| 2008/0156069 A1 | 7/2008 | Murata et al. | |
| 2015/0369643 A1 * | 12/2015 | Murata | ..................... G01F 1/56 |
| | | | 73/861.08 |

FOREIGN PATENT DOCUMENTS

| | | | |
|---|---|---|---|
| JP | 2008108765 A | | 5/2008 |
| JP | 2008159734 A | | 7/2008 |
| JP | 2010135387 A | | 6/2010 |
| JP | 2010147451 A | * | 7/2010 |
| JP | 2012114371 A | | 6/2012 |

* cited by examiner

*Primary Examiner* — Daniel J Colilla
(74) *Attorney, Agent, or Firm* — The Webb Law Firm

(57) ABSTRACT

An inspection apparatus used for an article storage facility includes an inactive gas supply portion provided with a supply nozzle provided in a placement support portion. A transport container having a supply port for an inactive gas is formed at a bottom portion thereof for accommodating substrates in a sealed state. The nozzle is joined to the supply port by a self weight of the transport container supported on the placement support portion so as to inject the inactive gas to an interior of the transport container. An inspection supply port is joined to the supply nozzle by a self weight of the inspection apparatus supported on the placement support portion, and is configured such that a gravity center position is supported on the placement support portion and coincides with a gravity center position of the transport container, the supply port inspects a state of supply of the inactive gas in the state of being supported on the placement support portion.

6 Claims, 8 Drawing Sheets

INSPECTION APPARATUS FOR ARTICLE STORAGE FACILITY

CROSS-REFERENCE TO RELATED APPLICATION

This application claims priority to Japanese Patent Application No. 2013-134265 filed Jun. 26, 2013, the disclosure of which is hereby incorporated in its entirety by reference.

FIELD OF THE INVENTION

The present invention relates to an inspection apparatus that is used for an article storage facility including a placement support portion on which a transport container having a supply port for an inactive gas formed at a bottom portion thereof for accommodating a substrate in a sealed state is placed and supported, and that inspects the state of supply of the inactive gas in a state in which the inspection apparatus is supported on the placement support portion.

BACKGROUND

In general, semiconductor elements are manufactured in a clean room whose internal atmosphere has been cleaned. Semiconductor wafers also need to be protected from contamination caused by the adhesion of impurities such as dirt and dust and a chemical reaction during the storage of semiconductor wafers that will serve as the material for the semiconductor elements and the transport of the semiconductor elements between the manufacturing steps. JP 2008-159734A discloses such a storage facility for storing semiconductor wafers. This storage facility includes storage racks including a plurality of storage sections that store air-tight transport containers such as a FOUP (Front Opening Unified Pod) for accommodating semiconductor wafers. Also, this storage facility has a purge function for supplying an inactive gas such as nitrogen or argon to the transport containers in order to prevent contamination caused by natural oxidation or the like of the semiconductor wafers accommodated in the transport containers.

Each transport container (storing FOUP) for accommodating semiconductor wafers includes a cover and a bottom surface portion that constitute a casing, and forms a sealed space by the cover and the bottom surface portion. A plurality of semiconductor wafers can be accommodated in the sealed space along the height direction. Recessed portions serving as a flow inlet and a flow outlet for gas are formed on the underside of the bottom surface portion, and the recessed portions are configured to be able to be joined to pipes of a purge unit that supplies an inactive gas. Placing a transport container on the purge unit causes the recessed portions and the pipes to be joined together, thereby enabling the inactive gas to be supplied to that transport container. Here, in order to confirm whether the inactive gas is appropriately supplied to the transport container, the flow rate of the inactive gas may be measured. In JP 2008-159734A, an inspection apparatus (measurement FOUP) is used for measuring the flow rate of the inactive gas. A flow inlet and a flow outlet capable of being joined to the pipes of the purge unit by placing the inspection apparatus on the purge unit are also formed on the bottom surface of the inspection apparatus (measurement FOUP). The inspection apparatus includes a flowmeter, and the flow rate of the inactive gas can be measured by placing the inspection apparatus on the purge unit, in place of the transport container (JP 2008-159734A: paragraphs 0032 to 0036, etc.).

SUMMARY OF THE INVENTION

As described above, the flow inlet and the flow outlet of the transport container and the inspection apparatus and the pipes of the purge unit are joined by the self weights of the transport container and the inspection apparatus. In other words, the joining strength varies depending on the masses or the gravity center positions of the transport container and the inspection apparatus. The mass or the gravity center position of the transport container varies depending on the number of semiconductor wafers accommodated therein. For example, when the number of semiconductor wafers accommodated is small, the weight of the transport container is small. When the weight of the transport container is smaller than that of the inspection apparatus, the joining strength of the transport container is relatively weak as compared with that of the inspection apparatus. In addition, as a result of variation in the gravity center position, the joining strength may become weaker or stronger. When the joining force is weak, there is the possibility that a gas leakage may occur between the purge unit and the transport container or the inspection apparatus. However, such a gas leakage cannot be taken into consideration when there is a large difference in joining force between the transport container and the inspection apparatus, and therefore, there is the possibility that the measurement accuracy of the flow rate may be reduced.

Thus, there is a need for the provision of a technique by which the flow rate of an inactive gas supplied to the transport container can be measured accurately.

According to an embodiment of the present invention, there is provided an inspection apparatus for an article storage facility, the article storage facility including:

a plurality of storage sections each including a placement support portion on which is placed and supported a transport container having a supply port for an inactive gas formed at a bottom portion thereof for accommodating a number of substrates that is less than or equal to a predetermined number of substrates in a sealed state, the storage sections being capable of storing the transport containers in a state in which the transport containers are supported on the placement support portions; and an inactive gas supply portion including a supply nozzle that is a nozzle provided in the placement support portion, and that is joined to the supply port by a self weight of the transport container supported on the placement support portion so as to inject the inactive gas to an interior of the transport container, wherein the inspection apparatus for the article storage facility is an apparatus for inspecting a state of supply of the inactive gas by the inactive gas supply portion in a state in which the inspection apparatus is supported on the placement support portion, and includes:

an inspection supply port that is joined to the supply nozzle by a self weight of the inspection apparatus supported on the placement support portion, wherein the inspection apparatus is configured such that a gravity center position of the inspection apparatus in a direction along a horizontal plane in the state in which the inspection apparatus is supported on the placement support portion coincides with a gravity center position of the transport container in a direction along a horizontal plane in the state in which the transport container is supported on the placement support portion.

With this configuration, the joining between the supply port and the supply nozzle is achieved by the self weight of the transport container in the state in which the transport container is supported on the placement support portion, and the joining between the inspection supply port and the supply nozzle is achieved by the self weight of the inspection apparatus in the state in which the inspection apparatus is supported on the placement support portion. Due to the gravity center position of the inspection apparatus in a direction along a horizontal plane in the state in which the inspection apparatus is supported on the placement support portion coinciding with the gravity center position of the transport container in a direction along the horizontal plane in the state in which the transport container is supported on the placement support portion, it is possible to reproduce the joining force according to at least the ratio between the weight of the transport container and the weight of the inspection apparatus. For example, when the supply nozzles are provided in a plurality of locations, it is also possible to suppress variation in joining force that could be caused by the difference in gravity center position (eccentricity), thus increasing the inspection accuracy. That is, with the present configuration, it is possible to provide a technique by which the flow rate of an inactive gas supplied to the transport container can be measured accurately.

Hereinafter, examples of preferred embodiments of the present invention will be described.

A flowmeter, an inspection controller, a power supply and so forth may also be mounted to an inspection apparatus. As described above, the joining between the inspection supply port and the supply nozzle is achieved by the self weight of the inspection apparatus in the state in which the inspection apparatus is supported on the placement support portion. Accordingly, in view of the achievement of an inspection under adverse conditions under which a gas leakage is more likely to occur (conditions under which the joining strength is reduced), it is preferable that the weight of the inspection apparatus is as small as possible.

In an embodiment of the inspection apparatus for an article storage facility according to the present invention, it is preferable that a weight of the inspection apparatus is smaller than a maximum weight that is a weight of the transport container when a maximum number of substrates are accommodated in the transport container.

In an embodiment of the inspection apparatus for an article storage facility according to the present invention, it is preferable that a weight of the inspection apparatus is less than or equal to a minimum weight that is a weight of the transport container when the transport container is in an empty state.

With the above-described configuration, the conditions under which the joining strength based on the self weight of the transport container in the state in which it is supported on the placement support portion is the smallest can be reproduced in the inspection apparatus.

Each transport container is configured to be able to accommodate a plurality of substrates. That is, the total weight of the transport container may take various values, ranging from the total weight of the transport container in an empty state in which not a single substrate is housed to the total weight of the transport container in a full load state in which the upper limit of a predetermined number of substrates are housed. Accordingly, the joining strength between the supply port and the supply nozzle also varies depending on the total weight of the transport container. For example, when the transport container is in the empty state, the total weight is the smallest and the joining strength is the weakest. On the other hand, when the transport container is in the full load state, the total weight of the transport container is the greatest and the joining strength is the strongest. Accordingly, it is preferable that an inspection can be performed by adjusting the weight of the inspection apparatus according to each of housing states of the transport container.

That is, in an embodiment of the inspection apparatus for an article storage facility according to the present invention, it is preferable that the inspection apparatus includes a weight supporting portion that supports a weight-adjusting weight.

In general, the gravity center position of the transport container in a direction along the horizontal direction does not coincide with the gravity center position of the substrate, and therefore, the gravity center position of the transport container in a direction along the horizontal direction varies depending on the number of substrates housed in the transport container. Accordingly, not only the weight of the transport container, but also the gravity center position thereof in a direction along the horizontal direction changes according to the housing state. When the gravity center position changes, the joining strength between the supply port and the supply nozzle also changes. Therefore, it is preferable that an inspection can be performed by also adjusting the gravity center position of the inspection apparatus in a direction along the horizontal direction according to each of the housing states.

That is, in an embodiment of the inspection apparatus for an article storage facility according to the present invention, it is preferable that a plurality of weight supporting portions that support weight-adjusting weights are disposed at positions different from the gravity center position of the inspection apparatus in a direction along a horizontal plane.

With this configuration, the gravity center position can be adjusted by disposing weights on the weight supporting portions in a plurality of locations.

DETAILED DESCRIPTION

Figure 1:
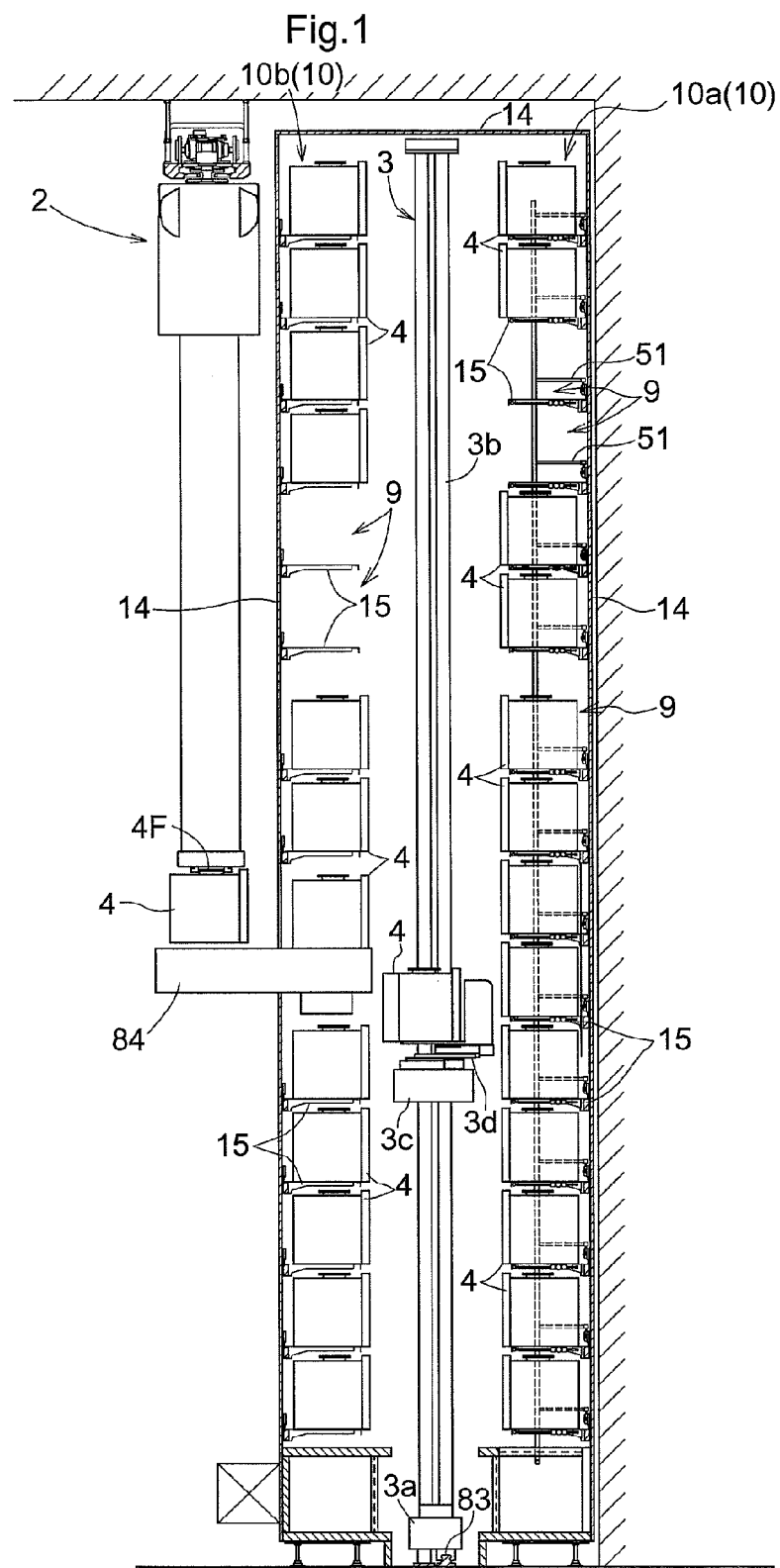
FIG. 1 is a longitudinal sectional side view showing the configuration of a substrate container storage facility.
Figure 2:
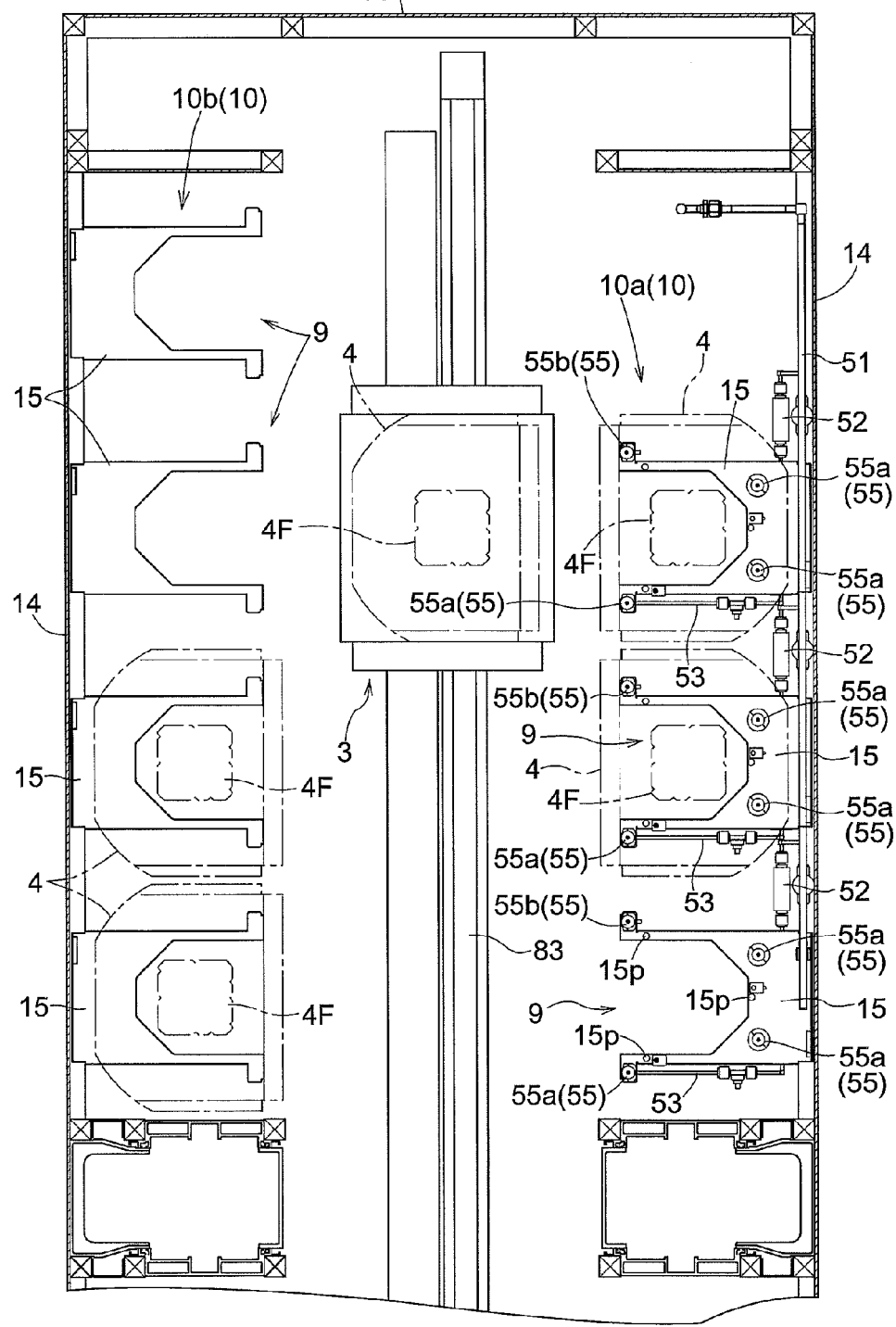
FIG. 2 is a partial plan view of the facility.

In the following, a description will be given of an embodiment in the case where the present invention is applied to an inspection apparatus for a substrate container storage facility with reference to the drawings. As shown in FIGS. 1 and 2, a substrate container storage facility (article storage facility)

includes storage racks 10 each including a plurality of storage sections 9 arranged in the vertical and lateral directions, the storage sections 9 being capable of storing containers 4 (transport containers) by including container support members 15 (placement support portions) that support the containers 4, and a stacker crane 3 that transfers the containers 4 by traveling on a traveling rail 83 provided in front of the storage racks 10. The stacker crane 3 includes a traveling truck 3*a* having a traveling wheel (not shown) rolling on the traveling rail 83, an elevating guide mast 3*b* provided upright on the traveling truck 3*a*, and an elevation platform 3*c* capable of moving up and down by being guided by the elevating guide mast 3*b*. The elevation platform 3*c* is provided with a SCARA arm-type transfer device 3*d* capable of transferring the container 4 between the elevation platform 3*c* and each container support member 15. The transfer device 3*d* can be switched in position between a retracted position to overlap the elevation platform 3*c* and a protruding position to protrude toward the container support member 15 in plan view (when viewed from a direction along the vertical direction) as shown in FIG. 2, and is thus configured to be capable of transferring the container 4.

A pair of storage racks 10 are provided in a configuration in which the front surfaces thereof are opposed to each other. One of the pair of the storage racks 10 is configured as a purge rack 10*a*, and the other is configured as a non-purge rack 10*b*. The purge rack 10*a* is a storage rack 10 that is provided with support member-side connecting portions 55. Here, each of the support member-side connecting portions 55 includes supply holes 55R1 for supplying an inactive gas such as a nitrogen gas to a container interior space 4S of the container 4 or a discharge hole 55R2 for discharging the gas within the container from the container interior space 4S to the outside in order to prevent the contamination of the semiconductor wafer within the container 4. On the other hand, the non-purge rack 10*b* is a storage rack 10 that is not provided with such a support member-side connecting portion 55. The transfer device 3*d* of the stacker crane 3 is capable of transferring the container 4 to both the container support member 15 of the purge rack 10*a* and the container support member 15 of the non-purge rack 10*b*.

The purge rack 10*a*, the non-purge rack 10*b*, and the stacker crane 3 are installed in the interior of a space surrounded by a wall member 14. Also, a storage and retrieval conveyor 84 that transports the container 4 between the exterior and the interior of the wall member 14 is provided through the wall member 14. The end portion of the storage and retrieval conveyor 84 on the outer side of the wall member 14 serves as a location where the storage and retrieval conveyor 84 passes and receives the container 4 to and from a hoist-type inter-facility container transport device 2. The end portion of the storage and retrieval conveyor 84 on the inner side of the wall member 14 serves as a location where the storage and retrieval conveyor 84 passes and receives the container 4 to and from the transfer device 3*d* of the stacker crane 3.

Figure 3:
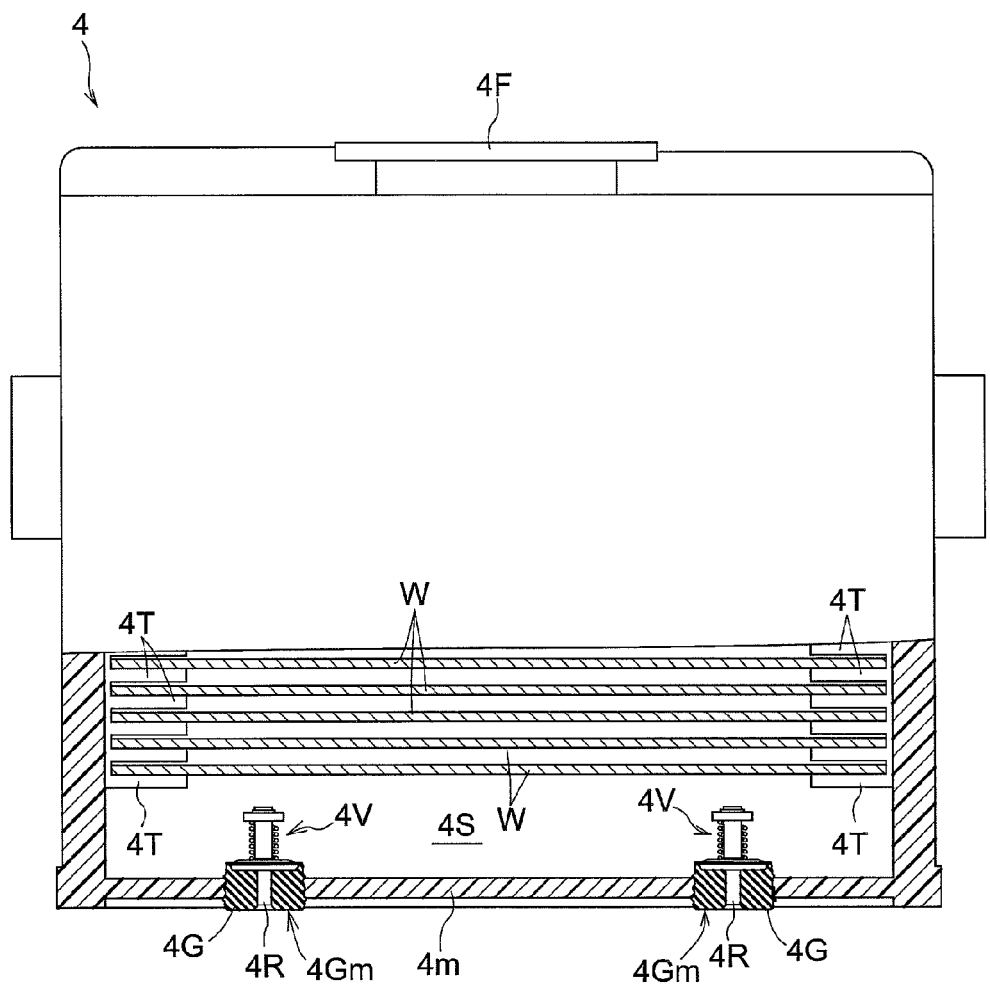
FIG. 3 is a partially cutout illustration of a container.

As shown in FIG. 3, the container 4 is an air-tight container made of synthetic resin that is compliant with the SEMI (Semiconductor Equipment and Materials International) standard. In the interior of the container 4 is provided a wafer support member 4T that supports the semiconductor wafer W (substrate) accommodated therein on both sides in the width direction from below. Here, a plurality of wafer support members 4T are arranged in the vertical direction with a predetermined interval therebetween, and thus the container 4 is configured to be able to accommodate a plurality of semiconductor wafers W. In the front surface of the container 4 is formed a substrate entrance opening that is opened/closed by a detachable cover member. On the top surface of the container 4 is formed a top flange 4F that is grasped by the inter-facility container transport device 2. Note that, for example, a FOUP (Front Opening Unified Pod) or the like for accommodating semiconductor wafers in a sealed state can be used as the container 4.

Figure 4:
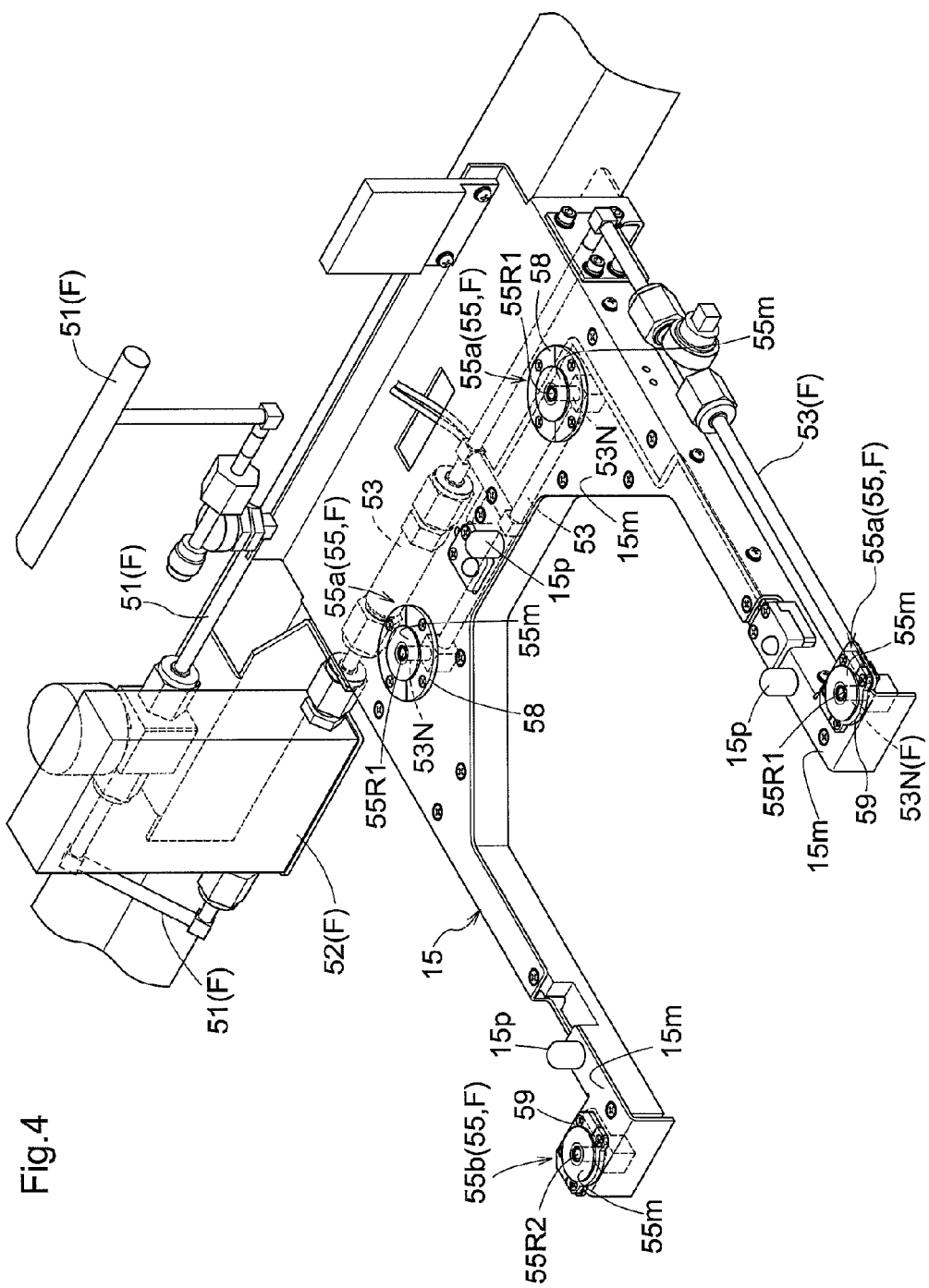
FIG. 4 is a perspective view of a container support member.

As shown in FIG. 4, the container support member 15 is formed in a U-shape in plan view to form a space through which the transfer device 3*d* passes up or down, and is equipped with positioning pins 15*p* in the upright condition in a plurality of (in the present example, three) locations on the top surface thereof. When the container 4 is transferred to the container support member 15, the elevation platform 3*c* is moved up such that the undersurface of the container 4 supported by the transfer device 3*d* is positioned at a height that is higher by a set height than that of the container support member 15 to which the container 4 is to be transferred, after that the position of the transfer device 3*d* is switched to the protruding position. Subsequently, the elevation platform 3*c* is moved down until the undersurface of the container 4 is positioned at a height that is lower by a set height than the height of the container support member 15 to which the container 4 is to be transferred. Thereby, the state of the container 4 is switched from a state in which it is supported by the transfer device 3*d* to a supported state in which it is supported by the container support member 15.

At a bottom portion 4*m* of the container 4 are provided a plurality of (in the present example, three) guiding recessed portions (not shown) with which a plurality of (in the present example, three) positioning pins 15*p* provided on the top surface of the container support member 15 are respectively engaged. Each of the guiding recessed portions is formed such that a part thereof that abuts against the upper end of the corresponding positioning pin 15*p* when the container 4 is at a set position is the deepest part, and the remaining part becomes gradually shallower so as to form a slope-shaped guided surface. Accordingly, as the container 4 is moved downward so as to be brought into the supported state in which it is supported on the container support member 15, the container 4 is gradually moved to the set position in a direction along a horizontal plane. Thereby, the container support member 15 supports the container 4 from below in the state in which the container 4 is aligned with the set position.

As shown in FIG. 3, at the bottom portion 4*m* of the container 4 are provided grommets 4G (supply port, exhaust port) as container-side connecting portions each having a communicating hole 4R capable of allowing communication between the container interior space 4S and the outside. Via the communicating hole 4R, an inactive gas (in the present example, a nitrogen gas) is supplied to the container interior space 4S. The grommet 4G is formed in a circular shape in plan view, and the communicating hole 4R is provided in the center of the circular shape in plan view. Also, a container-side joining surface 4Gm having a flat shape is formed around the communicating hole 4R on the undersurface of the grommet 4G. Note that an open/close valve mechanism 4V that is biased in the closing direction by biasing means such as a spring is provided in the interior of the grommet 4G. The open/close valve mechanism 4V is configured to be brought into the open state only when the pressure of the gas supplied via the communicating hole 4R or the gas discharged via the communicating hole 4R is greater than or equal to a set pressure.

A plurality of support member-side connecting portions 55 are provided in each of the container support members 15. In the present embodiment, as shown in FIG. 4, a total of four support member-side connecting portions 55, including two on the rack back side and two on the rack front side when viewed from the rack front, are provided in each of the container support members 15. Two support member-side connecting portions 55 on the rack back side and one support member-side connecting portion 55 on the rack right front side are first support member-side connecting portions 55a each including a supply hole 55R1 for supplying the inactive gas to the container interior space 4S of the container 4. One support member-side connecting portion 55 on the rack left front side is a second support member-side connecting portion 55b including a discharge hole 55R2 for discharging a gas from the container interior space 4S.

As shown in FIG. 4, a supply pipe 51 for supplying the inactive gas is separately provided in each of the container support members 15 of the purge rack 10a, and the supply pipe 51 is connected to a flow inlet-side connecting portion of a supply flow rate adjustment device 52. A container supply pipe 53 is connected to a flow outlet-side connecting portion of the supply flow rate adjustment device 52. The container supply pipe 53 is connected to a supply nozzle 53N protruding upward from a top surface 15m of the container support member 15 at the installation position of the first support member-side connecting portion 55a in the container support member 15, and is configured such that the inactive gas is ejected from the supply nozzle 53N.

Additionally, a discharge nozzle (not shown) protruding upward from the top surface 15m of the container support member 15 is provided at the installation position of the second support member-side connecting portion 55b in the container support member 15. The protruding height (the vertical dimension of the protruding portion) of the discharge nozzle from the top surface 15m of the container support member 15 is the same as the protruding height of the supply nozzle 53N from the top surface 15m of the container support member 15. Further, the downstream side of the discharge nozzle in the gas passage direction is open, and the gas from the container interior space 4S of the container 4 is released from this opening. The supply pipe 51, the supply flow rate adjustment device 52, the container supply pipe 53, the supply nozzle 53N, and the support member-side connecting portion 55 constitute an inactive gas supply portion F.

Each supply hole 55R1 is configured such that the supply nozzle 53N is slidably fitted therewith, and the inactive gas is ejected through the supply hole 55R1. The discharge hole 55R2 is configured such that the discharge nozzle is slidably fitted therewith, and the gas is discharged from the container interior space 4S through the discharge hole 55R2. The vertical dimensions of the part where the supply hole 55R1 is formed and the part where the discharge hole 55R2 is formed in the support member-side connecting portion 55 are configured to be larger than at least the protruding height of the supply nozzle 53N and the discharge nozzle from the top surface 15m of the container support member 15. Note that the first support member-side connecting portion 55a and the second support member-side connecting portion 55b have the same configuration, and thus are simply described as the support member-side connecting portion 55 in the following description, unless it is necessary to make a distinction therebetween.

Figure 5:
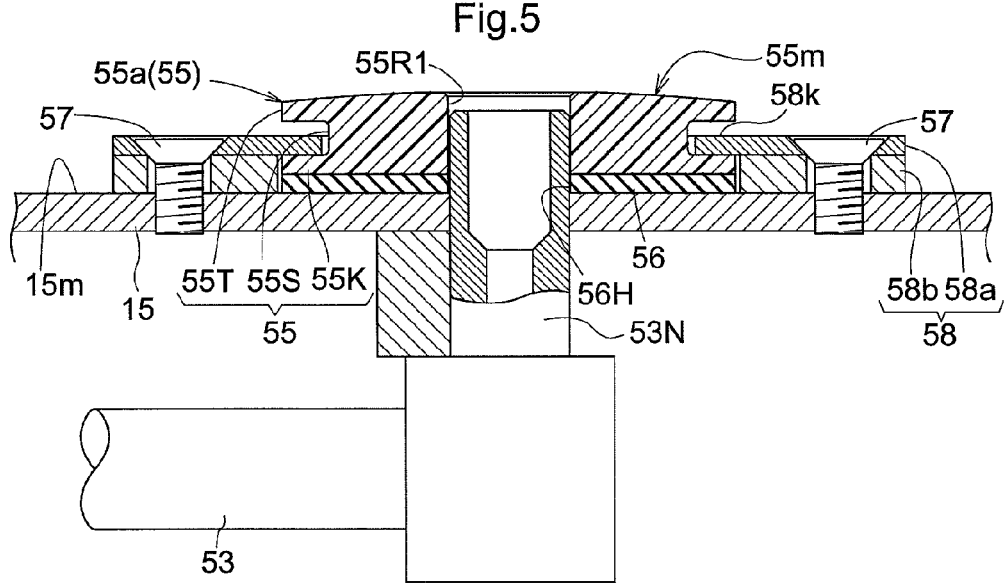
FIG. 5 is a broken-away side view of a support member-side connecting portion.
Figure 6:
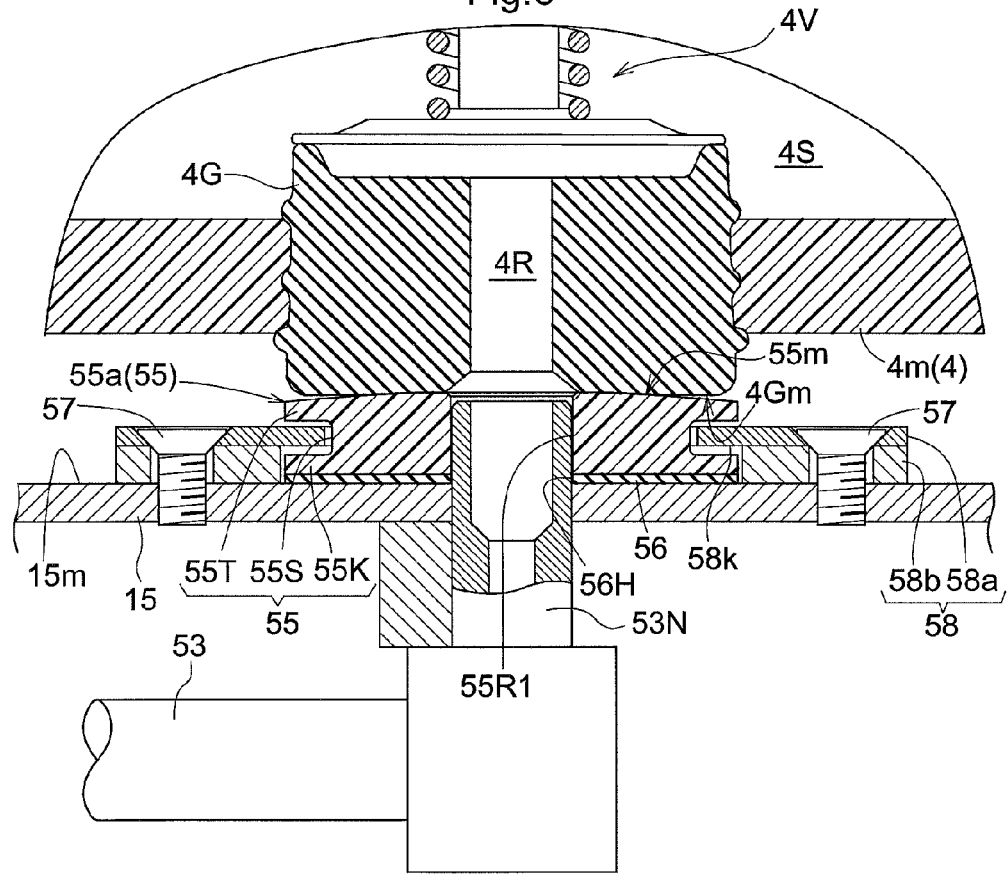
FIG. 6 is a diagram illustrating the states of a grommet and the support member-side connecting portion in a supported state.

The support member-side connecting portion 55 is made of tubular polytetrafluoroethylene (PTFE), and is formed in a circular shape in plan view as shown in FIGS. 5 and 6. Further, the support member-side connecting portion 55 is configured such that the container-side joining surface 4Gm, which is the undersurface of the grommet 4G, and a support member-side joining surface 55m, which is the top surface of the support member-side connecting portion 55, are joined in the supported state in which the container 4 is supported on the container support member 15, and the supply hole 55R1 is in communication with the communicating hole 4R at this time (the same also applies to the discharge hole 55R2). The support member-side joining surface 55m is formed in a shape along a spherical surface that is upwardly convex. In other words, the support member-side joining surface 55m is formed in a shape that gradually extends downward as it is separated from the supply hole 55R1 or the discharge hole 55R2.

As shown in FIG. 5, the support member-side connecting portion 55 includes a head part 55T, a reduced diameter part 55S, and a leg part 55K. The head part 55T is a part including the support member-side joining surface 55m. The reduced diameter part 55S is a part that has a diameter smaller than that of the head part 55T and larger than that of the supply hole 55R1 or the discharge hole 55R2, and that is formed below and in contact with the head part 55T. The leg part 55K is a part that has a diameter larger than that of the reduced diameter part 55S and is formed below and in contact with the reduced diameter part 55S.

For example, as shown in FIG. 5, the support member-side connecting portion 55 is attached to the top surface 15m of the container support member 15 by using attachment members 58. Each of the attachment members 58 is composed of a first attachment member 58a and a second attachment member 58b that are plate-shaped members having a ring shape in plan view. Note that, as shown in FIG. 4, the support member-side connecting portions 55 on the back side of the U-shaped container support member 15 are attached to the top surface 15m of the container support member 15 by using the attachment members 58, and the support member-side connecting portions 55 on the opening portion side are attached to the top surface 15m of the container support member 15 by using attachment members 59. Although the shapes of the attachment members (58, 59) differ depending on the attachment portions of the support member-side connecting portions 55, the attachment dimension, the attachment method and the like of the attachment members are the same.

An elastic member 56 is interposed between each support member-side connecting portion 55 and the container support member 15. The elastic member 56 is constituted by a ring-shaped rubber sheet (a material having a smaller elastic modulus than that of PTFE, which is the material of the support member-side connecting portion 55) having a small thickness and a hole portion 56H for passage of the supply nozzle 53N at the center thereof. The hole portion 56H is formed such that its radial dimension is the same as the tube outer diameter of the supply nozzle 53N, or slightly smaller than the tube outer diameter of the supply nozzle 53N. The support member-side connecting portion 55 is attached to the container support member 15, with the supply nozzle 53N passing through the hole portion 56H of the elastic member 56 and the undersurface of the elastic member 56 abutting against the top surface 15m of the container support member 15. As shown in FIG. 5, the attachment member 58 is fastened to the container support member 15 by using screws 57, with the first attachment member 58a fitted with the reduced diameter part 55S of the support member-side connecting portion 55. Thus, the support member-side connecting portion 55 is attached to the container support member 15 so as not to move from a predetermined position of the container support member 15 in plan view, while being allowed to move vertically a distance corresponding to the difference between the vertical dimension of the first attachment member 58a and the vertical dimension of the reduced diameter part 55S.

FIG. 6 shows the states of the grommet 4G and the support member-side connecting portion 55 in the supported state in which the container 4 is supported on the container support member 15. In the supported state of the container 4, the supply nozzle 53N (also including the discharge nozzle) and the grommet 4G are joined by the self weight of the container 4. As described above, the elastic member 56 is provided below the support member-side connecting portion 55, and the support member-side connecting portion 55 is biased to the upper side while being allowed to move vertically. Accordingly, it is possible to achieve a state in which the container-side joining surface 4Gm, which is the undersurface of the grommet 4G, and the support member-side joining surface 55m, which is the top surface of the support member-side connecting portion 55, are joined appropriately. As described above, the open/close valve mechanism 4V is biased in the closing direction by biasing means such as a spring, and is brought into the open state only when the pressure of the gas supplied via the communicating hole 4R or the gas discharged via the communicating hole 4R is greater than or equal to the set pressure. Due to the container-side joining surface 4Gm and the support member-side joining surface 55m being appropriately joined, it is possible to supply the gas to the interior of the container 4 or discharge the gas from the interior of the container 4 to the outside, while inhibiting leakage.

Figure 7:
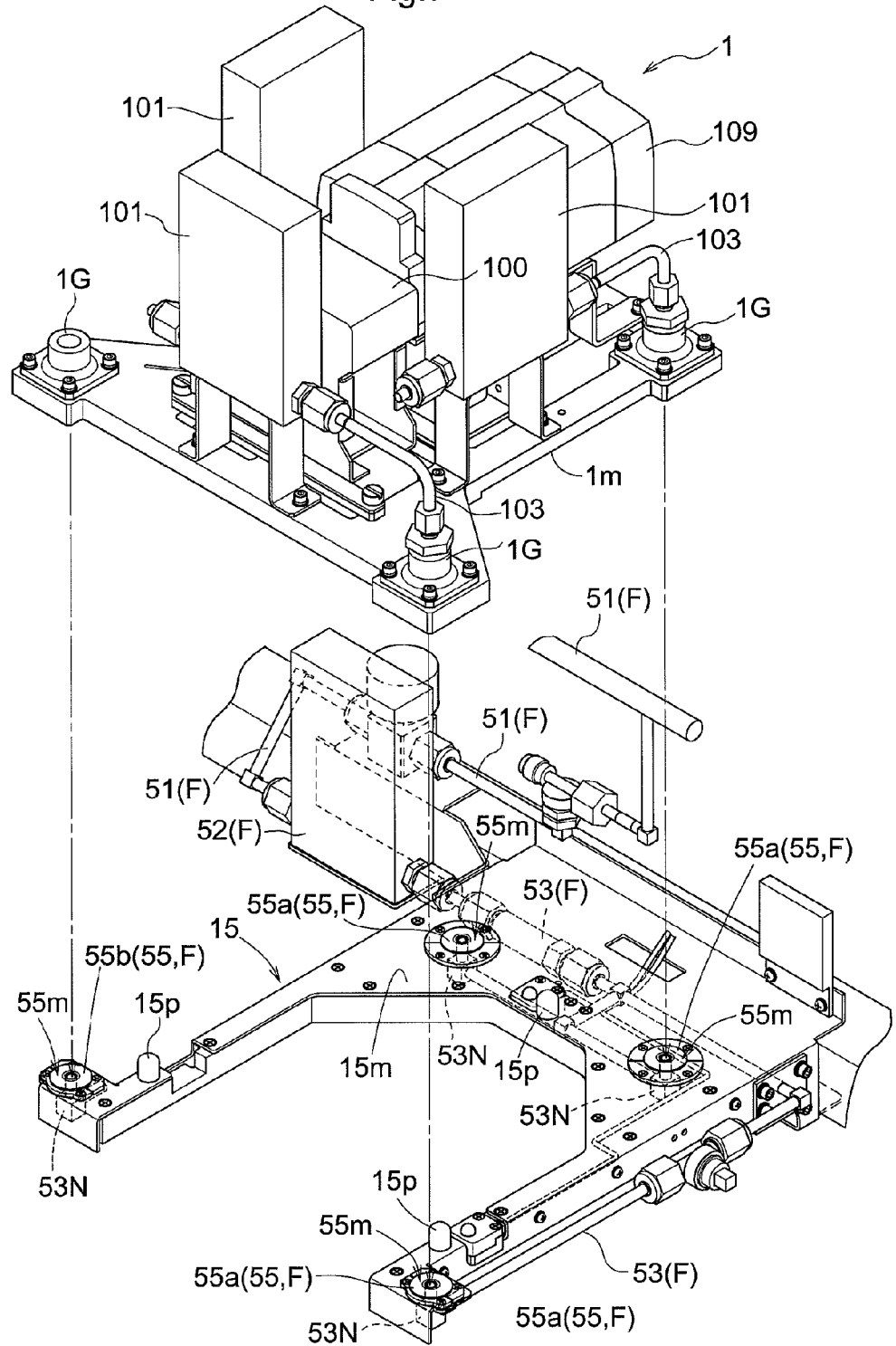
FIG. 7 is a perspective view showing a method for placing an inspection apparatus on the container support member.

In order to confirm whether the semiconductor wafers W can be appropriately protected from contamination caused by the adhesion of impurities such as dirt and dust and a chemical reaction during the storage of the semiconductor wafers W that will serve as the material for semiconductor elements and the transport of the semiconductor elements between the manufacturing steps, the substrate container storage facility is also subjected to an inspection. As such an inspection, the supply flow rate of the inactive gas is measured in order to confirm whether the inactive gas is appropriately supplied to the container 4. For example, as shown in FIG. 7, the state of supply of the inactive gas is inspected by using an inspection apparatus 1 that is supported on the container support member 15 in place of the container 4. The inspection apparatus 1 is configured according to specifications corresponding to the container 4 compliant with the SEMI standard. Specifically, the inspection apparatus 1 is configured such that the specifications of parts coming into contact with the container support member 15, including, for example, the correspondence with the positioning pin 15p and the method for joining to the support member-side connecting portion 55 are the same as those of the container 4.

Figure 8:
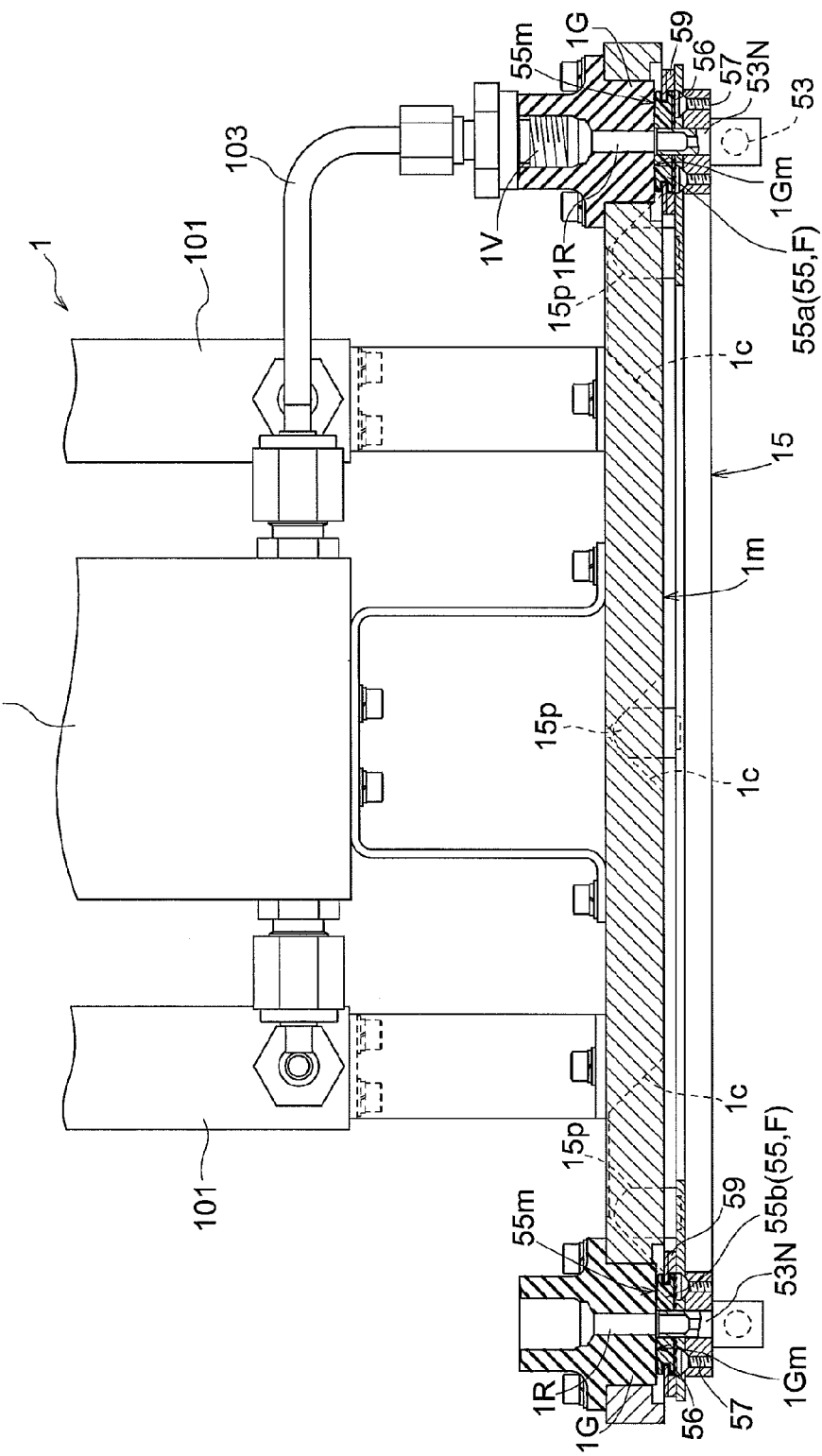
FIG. 8 is a longitudinal sectional side view of the container support member in a state in which an inspection apparatus is placed thereon.

As described above, three guiding recessed portions with which the three positioning pins 15p provided on the top surface of the container support member 15 are respectively engaged are formed in the bottom portion 4m of the container 4. Likewise, a plurality of (in the present example, three) guiding recessed portions 1c with which the positioning pins 15p are respectively engaged are formed in the bottom portion 1m of the inspection apparatus 1 (see FIG. 8). Each of the guiding recessed portions 1c is formed such that a part thereof that abuts against the upper end of the corresponding positioning pin 15p when the inspection apparatus 1 is at the same set position as that of the container 4 is the deepest part, and the remaining part becomes gradually shallower so as to form a slope-shaped guided surface. In other words, the inspection apparatus 1 is supported from below by the container support member 15 in the same state as the state in which the container 4 is aligned with the set position.

Additionally, inspection grommets 1G (inspection supply ports) similar to the grommets 4G of the container 4 are provided in the bottom portion of the inspection apparatus 1. While the grommets 4G of the container 4 each include the communicating hole 4R capable of allowing communication between the container interior space 4S and the outside, the inspection grommets 1G each include an inspection communicating hole 1R capable of being in communication with a flowmeter 101 via an inspection pipe 103. Via the inspection communicating hole 1R, the inactive gas is supplied to the flowmeter 101. The inspection communicating hole 1R is provided at the center of the inspection grommet 1G that is formed in a circular shape in plan view as with the grommet 4G. Additionally, on the undersurface of the inspection grommet 1G, an inspection apparatus-side joining surface 1G-m having a flat shape is formed around the inspection communicating hole 1R as with the grommet 4G of the container 4.

Note that an inspection open/close valve mechanism 1V that is biased in the closing direction by biasing means such as a spring is provided in the interior of the inspection grommet 1G. The inspection open/close valve mechanism 1V is configured to be brought into the open state only when the pressure of the gas supplied via the inspection communicating hole 1R or the gas discharged via the inspection communicating hole 1R is greater than or equal to a set pressure. The specifications of the inspection open/close valve mechanism 1V are also the same as those of the container 4. That is, the inspection apparatus 1 is connected to the support member-side connecting portions 55 in the same connection configuration of that of the container 4 when it is placed on the container support member 15.

Additionally, an inspection controller 100 that performs determination based on a measurement result obtained by the flowmeter 101 and stores the measurement result and the determination result is mounted to the inspection apparatus 1. Since the inspection apparatus 1 needs to be able to be placed on the container support member 15 in place of the container 4, the electric power for driving the inspection apparatus 1 including, for example, the inspection controller 100, is supplied from a battery 109 mounted to the inspection apparatus 1.

As described above, the supply nozzle 53N (also including the discharge nozzle) and the grommet 4G are joined by the self weight of the container 4 in the supported state in which the container 4 is supported on the container support member 15. The joining strength between the container-side joining surface 4Gm, which is the undersurface of the grommet 4G, and the support member-side joining surface 55m, which is the top surface of the support member-side connecting portion 55, is dependent on the total weight of the container 4. As described above with reference to FIG. 3, the container 4 includes a plurality of the wafer support members 4T that are arranged in the vertical direction, and each of the wafer support members 4T supports the accommodated semiconductor wafers W on both sides in the width direction from below. Accordingly, the container 4 is configured to be able to accommodate a plurality of semiconductor wafers W. That is, the total weight of the container 4 may take various values, ranging from the total weight of the container 4 in an empty state in which not a single semiconductor wafer W is housed to the total weight of the container 4 in a full load state in which semiconductor wafers W are housed in all of the wafer support members 4T. Accordingly, the joining strength between the container-side joining surface 4Gm and the support member-side joining surface 55m also varies depending on the total weight of the container 4. For example, when the container 4 is in the empty state, the total weight of the container 4 is the smallest and the joining strength is the weakest. On the other hand, when the container 4 is in the full load state, the total weight of the container 4 is the greatest and the joining strength is the strongest.

In general, the gravity center position of the container 4 in plan view (in a direction along the horizontal direction) does not coincide with the gravity center position of each of the semiconductor wafers W. Accordingly, the gravity center position of the container 4 in a direction along the horizontal direction varies depending on the number of semiconductor wafers W housed in the container 4. Accordingly, at the support member-side connecting portions 55, which are provided in four locations in the present embodiment, the joining strength between the container-side joining surface 4Gm and the support member-side joining surface 55m undergoes different changes as a result of the change in the gravity center position.

The magnitude of the joining strength affects the supply efficiency of the inactive gas. When the joining strength is weak, there is the possibility that the air tightness between the container-side joining surface 4Gm and the support member-side joining surface 55m may be reduced, resulting in a leakage. In view of cases where such a leakage occurs, the inspection apparatus 1 is required to measure the flow rate of the inactive gas according to the state of the container 4. Therefore, the inspection apparatus 1 is configured such that at least the gravity center position G (see FIG. 9) in a direction along a horizontal plane in the supported state in which it is supported on the container support member 15 coincides with the gravity center position of the container 4 along a horizontal plane in the supported state in which the container 4 is supported on the container support member 15. The gravity center position G is a gravity center position when the weight of the container 4 and the weight of the inspection apparatus 1 substantially match.

Also, the weight when the gravity center positions are aligned is preferably the weight when the container 4 is in the empty state, or in other words, a minimum weight of the container 4. That is, the state in which the weight of the container 4 is the smallest and the joining strength between the container-side joining surface 4Gm and the support member-side joining surface 55m is the weakest can be reproduced by using the inspection apparatus 1. Note that it is possible to increase the weight of the inspection apparatus 1 by adding a weight or the like to the inspection apparatus 1, and therefore, the weight of the inspection apparatus 1 does not need to match the minimum weight and may be less than the minimum weight.

As described above, in addition to the flowmeter 101, the inspection controller 100 and the battery 109 are also mounted to the inspection apparatus 1. Accordingly, there is the possibility that the weight of the inspection apparatus 1 may be greater than the weight of the container 4 in the empty state. However, in view of the joining strength between the container-side joining surface 4Gm and the support member-side joining surface 55m, it is desirable that the weight of the inspection apparatus 1 be as small as possible. Accordingly, the weight of the inspection apparatus 1 is preferably at least smaller than a maximum weight that is the weight of the container 4 when a maximum number of semiconductor wafers W are accommodated in the container 4. In this case, the state in which the container 4 is in the empty state cannot be reproduced, but the inspection accuracy can be increased by aligning the gravity center positions at least along a horizontal plane.

As described above, the total weight of the container 4 may take various values, ranging from the total weight of the container 4 in the empty state in which not a single semiconductor wafer W is housed to the total weight of the container 4 in the full load state in which semiconductor wafers W are housed in all of the wafer support members 4T. Therefore, it is preferable that an inspection using the inspection apparatus 1 can be performed in each of these states. For example, it is preferable that the inspection apparatus 1 is configured such that the weight thereof can be adjusted by adding a weight or the like thereto.

Figure 9:
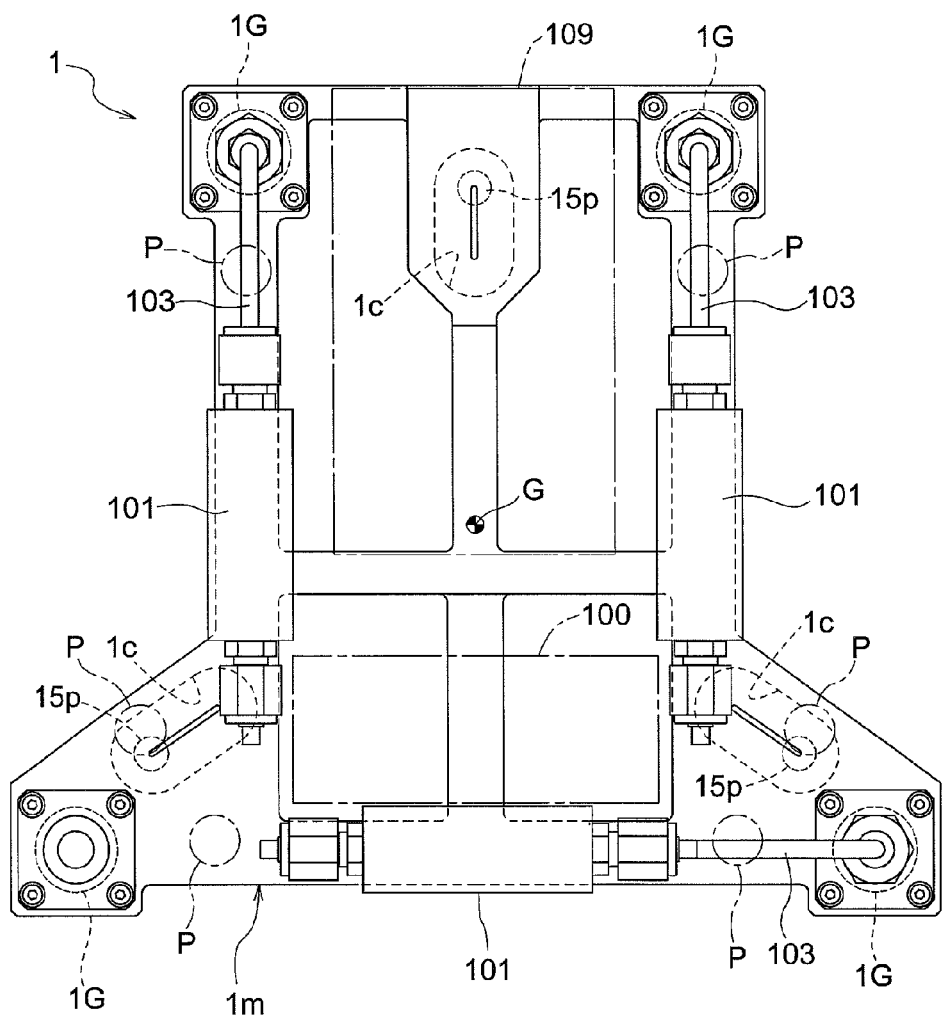
FIG. 9 is a plan view of the inspection apparatus.

For example, as shown in FIG. 9, it is preferable that the inspection apparatus 1 is provided with a weight supporting portion P that supports a weight-adjusting weight. While the present embodiment illustrates a configuration in which six weight supporting portions P are provided on the floor of the inspection apparatus 1, any number of weight supporting portions P may be installed. However, the gravity center position G can be adjusted by installing the weight supporting portions P in a plurality of locations. When the weight supporting portion P is installed in one location, it is preferable that the weight supporting portion P is installed at the gravity center position G in order to inhibit significant fluctuations of the gravity center position G by the addition of the weight. Although the present embodiment illustrates a configuration in which the weight supporting portions P are provided on the floor of the inspection apparatus 1, it is possible to adopt a configuration in which the weight is held in a suspended state.

The invention claimed is:

1. An article storage facility including an inspection apparatus, the article storage facility comprising:
   a plurality of storage sections each including a placement support portion on which is placed and supported a transport container having a supply port for an inactive gas formed at a bottom portion thereof, the transport container provided for accommodating a number of substrates that is less than or equal to a predetermined number of substrates in a sealed state, the storage sections being capable of storing the transport containers in a state in which the transport containers are supported on the placement support portions;
   an inactive gas supply portion including a supply nozzle that is a nozzle provided in the placement support portion, and that is joined to the supply port by a self weight of the transport container supported on the placement support portion so as to inject the inactive gas to an interior of the transport container, and
   an inspection apparatus for inspecting a state of supply of the inactive gas by the inactive gas supply portion in a state in which the inspection apparatus is supported on the placement support portion,
   wherein the placement support portion includes a plurality of support member-side connecting portions provided with the supply nozzle or a discharge nozzle for releasing the inactive gas from the interior of the transport container, and a plurality of engaging portions engageable with the bottom portion of the transport container, and
   wherein the inspection apparatus comprises:
   an inspection supply port that is joined to the supply nozzle by a self weight of the inspection apparatus supported on the placement support portion, a plate-shaped element supported only by the plurality of support member-side connecting portions and the plurality of engaging portions with the inspection apparatus being supported on the placement support portion, and a flowmeter, an inspection controller, and a battery mounted on the plate-shaped element, and wherein the inspection apparatus is configured such that a gravity center position of the inspection apparatus in a direction along a horizontal plane in the state in which the inspection apparatus is supported on the placement support portion coincides with a gravity center position of the transport container in a direction along a horizontal plane in the state in which the transport container is supported on the placement support portion.

2. The article storage facility according to claim 1, wherein a weight of the inspection apparatus is smaller than a maximum weight that is a weight of the transport container when a maximum number of substrates are accommodated in the transport container.

3. The article storage facility according to claim 1, wherein a weight of the inspection apparatus is less than or equal to a minimum weight that is a weight of the transport container when the transport container is in an empty state.

4. The article storage facility according to claim 1, wherein the inspection apparatus comprises a weight supporting portion that supports a weight-adjusting weight.

5. The article storage facility according to claim 4, wherein a plurality of the weight supporting portions are disposed at positions different from the gravity center position of the inspection apparatus in a direction along the horizontal plane.

6. The article storage facility according to claim 4, wherein a plurality of the weight supporting portions are arranged along peripheral edge portions of the plate-shaped element as viewed from the top.

\* \* \* \* \*